(12) United States Patent
Vallone

(10) Patent No.: US 7,957,984 B1
(45) Date of Patent: Jun. 7, 2011

(54) DEVICE FOR FACILITATING COMPLIANCE WITH MEDICATION REGIMEN

(76) Inventor: Anthony Vallone, Canton, OH (US)

( * ) Notice: Subject to any disclaimer, the term of this patent is extended or adjusted under 35 U.S.C. 154(b) by 690 days.

(21) Appl. No.: 11/712,376

(22) Filed: Feb. 28, 2007

(51) Int. Cl.
*G06Q 10/00* (2006.01)
*G06Q 50/00* (2006.01)

(52) U.S. Cl. .......................................................... 705/2

(58) Field of Classification Search .................. 705/2–3
See application file for complete search history.

(56) References Cited

U.S. PATENT DOCUMENTS

| | | | |
|---|---|---|---|
| 3,815,780 A | 6/1974 | Bauer | |
| 4,674,652 A * | 6/1987 | Aten et al. | 221/3 |
| 4,695,954 A * | 9/1987 | Rose et al. | 221/15 |
| 4,731,726 A * | 3/1988 | Allen, III | 600/300 |
| 5,347,453 A * | 9/1994 | Maestre | 705/2 |
| 5,642,731 A | 7/1997 | Kehr | |
| 5,691,932 A | 11/1997 | Reiner et al. | |
| 6,075,755 A | 6/2000 | Zarchan | |
| 6,188,648 B1 | 2/2001 | Olsen | |
| 6,909,359 B1 * | 6/2005 | McGovern | 340/309.16 |
| 7,155,306 B2 | 12/2006 | Haitin et al. | |
| 7,158,011 B2 * | 1/2007 | Brue | 340/309.16 |
| 7,188,738 B2 | 3/2007 | Stafford et al. | |
| 7,204,823 B2 * | 4/2007 | Estes et al. | 604/65 |
| 7,213,721 B2 | 5/2007 | Abdulhay et al. | |
| 7,353,939 B2 | 4/2008 | Coe et al. | |
| 7,359,765 B2 | 4/2008 | Varvarelis et al. | |
| 7,366,285 B2 * | 4/2008 | Parolkar et al. | 379/88.17 |
| 7,366,675 B1 | 4/2008 | Walker et al. | |
| 2001/0028308 A1 | 10/2001 | De La Huerga | |
| 2003/0216624 A1 * | 11/2003 | Lin et al. | 600/300 |
| 2004/0172295 A1 * | 9/2004 | Dahlin et al. | 705/2 |
| 2006/0155542 A1 * | 7/2006 | Vimegnon et al. | 704/260 |
| 2006/0218011 A1 | 9/2006 | Walker et al. | |
| 2008/0077439 A1 * | 3/2008 | Guion | 705/2 |

OTHER PUBLICATIONS

Non-Final Office Action cited in related U.S. Appl. No. 11/712,357 dated Mar. 27, 2009.
Non-Final Office Action cited in related U.S. Appl. No. 11/712,357 dated Oct. 20, 2009.
Non-Final Office Action cited in related U.S. Appl. No. 11/712,357 dated Mar. 19, 2010.
Non-Final Office Action cited in related U.S. Appl. No. 11/712,357 dated Aug. 13, 2010.
Notice of Allowance cited in related U.S. Appl. No. 11/712,357 dated Dec. 14, 2010.

* cited by examiner

*Primary Examiner* — Gerald J. O'Connor
*Assistant Examiner* — Sheetal R Rangrej
(74) *Attorney, Agent, or Firm* — Cooper Legal Group, LLC

(57) ABSTRACT

A device and method for facilitating compliance with a medication regimen are disclosed. The device incorporates an icon set that illustrates concepts relating to the medication regimen in a pictographic form that is easily recognized and comprehended. The device is programmed with medication instructions, and generates medication reminders for the medication instructions by displaying icons from the icon set. The device may additionally display text, play audio, vibrate, send text messages to other devices, etc. The device may accept input from the individual and/or caregiver regarding the medication instructions or the medication events. The device may also contain the medication, control access and dosing of the medication, and administer the medication to the individual. The device may also communicate information regarding the medication regimen to the caregiver, such as prescription renewal requests. This device and method may improve the accuracy and thoroughness of compliance and communication regarding the medication regimen.

27 Claims, 7 Drawing Sheets

DEVICE FOR FACILITATING COMPLIANCE WITH MEDICATION REGIMEN

FIELD

The present disclosure relates generally to the field of medication, and particularly to patient compliance with a medication regimen.

BACKGROUND

The medical community notes that medication errors are a major reason for patient hospitalization, with mortality estimates sometimes reported ats accounting for over 90,000 deaths per year. Although there are numerous factors contributing to this crisis, baselines in health-related information creation, transfer, comprehension, and compliance are key elements of this problem.

In efforts to address this problem, the medical community is embracing the advancement of computer-based systems. Although these systems are moving into the forefront, they may not be fully efficient or effective and may exhibit the same problems inherent in a paper-based system, including increased user entry and retrieval time in searching for current and historical i health-related information. Both systems exhibit common problems by relying on text-based communication, which may be ambiguous, region-specific, and either partly or fully miscomprehended by people interacting with the system. These problems may be exacerbated or compounded during the transfer of health-related information among healthcare professionals, due to the lack of standardization (resulting in "re-entry" errors) and comprehension issues, where content of material and interpretation of health-related information is variable, based on organizational and cognitive abilities.

The transfer of health-related information between the medical community and the general population also continues to have serious problems, since non-standardized and often incomplete health-related information may be imperfectly "pieced together" by multiple healthcare providers and the patient to create an incorrect or incomplete medical record. This problem may also arise when health-related information (including the vehicle, route, dosage, time of day, administration, and/or use of a medication) is not easily transferred, accessed, or understood by the general population.

Improvements in the process of recording and communicating medical information, including medication regimen information, are therefore desirable.

SUMMARY

The following presents a simplified summary of the disclosure in order to provide a basic understanding of some aspects of the disclosure. This summary is not an extensive overview of the disclosure. It is intended neither to identify key or critical elements of the disclosure nor to delineate the scope of the disclosure. Rather, its primary purpose is merely to present one or more concepts of the disclosure in a simplified form as a prelude to the more detailed description that is presented later.

The present disclosure relates to a device for recording and communicating health-related information, including medication regimen information. The device relies on an icon set that illustrates the concepts relating to the health-related information, including the medication regimen, in a pictographic form that is easy for the individual to recognize and comprehend. The present disclosure also relates to a method of facilitating individual compliance with a medication regimen through the utilization of such a device.

The use of a medical icon set for communicating health-related information has many potential advantages. First, the individual may comprehend the reminder message in a language-independent manner. Pictographic icons can be used to circumvent differences in language capabilities and skill levels among the caregivers and the individual. The icon set may be cognizable to individuals with limited literacy skills or with mental faculties, such as very young, elderly, and mentally handicapped individuals.

Second, if a common set of medical icons is utilized by many caregivers and individuals, it may become a standard and standardized lexicon for the communication of health-related information, including medication regimen information. Regular and frequent exposure to the same icon set, especially from a variety of sources, may lead to quicker, fuller, and more accurate recognition and comprehension by caregivers and individuals of these icons and the illustrated concepts. Moreover, widespread exposure to and use of the same icon set may improve the speed, depth, and precision of communication of health-related information among many caregivers and individuals.

Many such icon sets may be conceptualized to represent many areas of healthcare. However, the present disclosure addresses the administration of medication, and the concepts related thereto.

In furtherance of these advantages, the present disclosure recommends the use of a medication device that functions as a medication reminder for the individual. Both the device and its use in a method of facilitating medication regimen compliance are contemplated by the disclosure. The medication device includes a medication regimen icon set, and predominantly communicates with the individual regarding medication instructions through the display of icons chosen from this icon set. Once a medication regimen has been formulated, the device is programmed with one or more medication instructions that comprise a medication regimen. The device may include a chronometer, by which it monitors time, and logic for determining when to generate medication reminder messages based on the chronometer and the medication instructions. For each medication instruction, and more specifically for each medication event corresponding to each medication instruction, the device generates a medication reminder message by displaying icons that are representative of the medication instruction.

The medication device may optionally exhibit other features to facilitate compliance with the medication regimen and completion of the medical record. These options will be discussed in detail hereinbelow.

To the accomplishment of the foregoing and related ends, the following description and annexed drawings set forth in detail certain illustrative aspects and implementations of the disclosure. These are indicative of but a few of the various ways in which one or more aspects of the present disclosure may be employed. Other aspects, advantages and novel features of the disclosure will become apparent from the following detailed description when considered in conjunction with the annexed drawings.

DEFINITIONS

Figure 1:
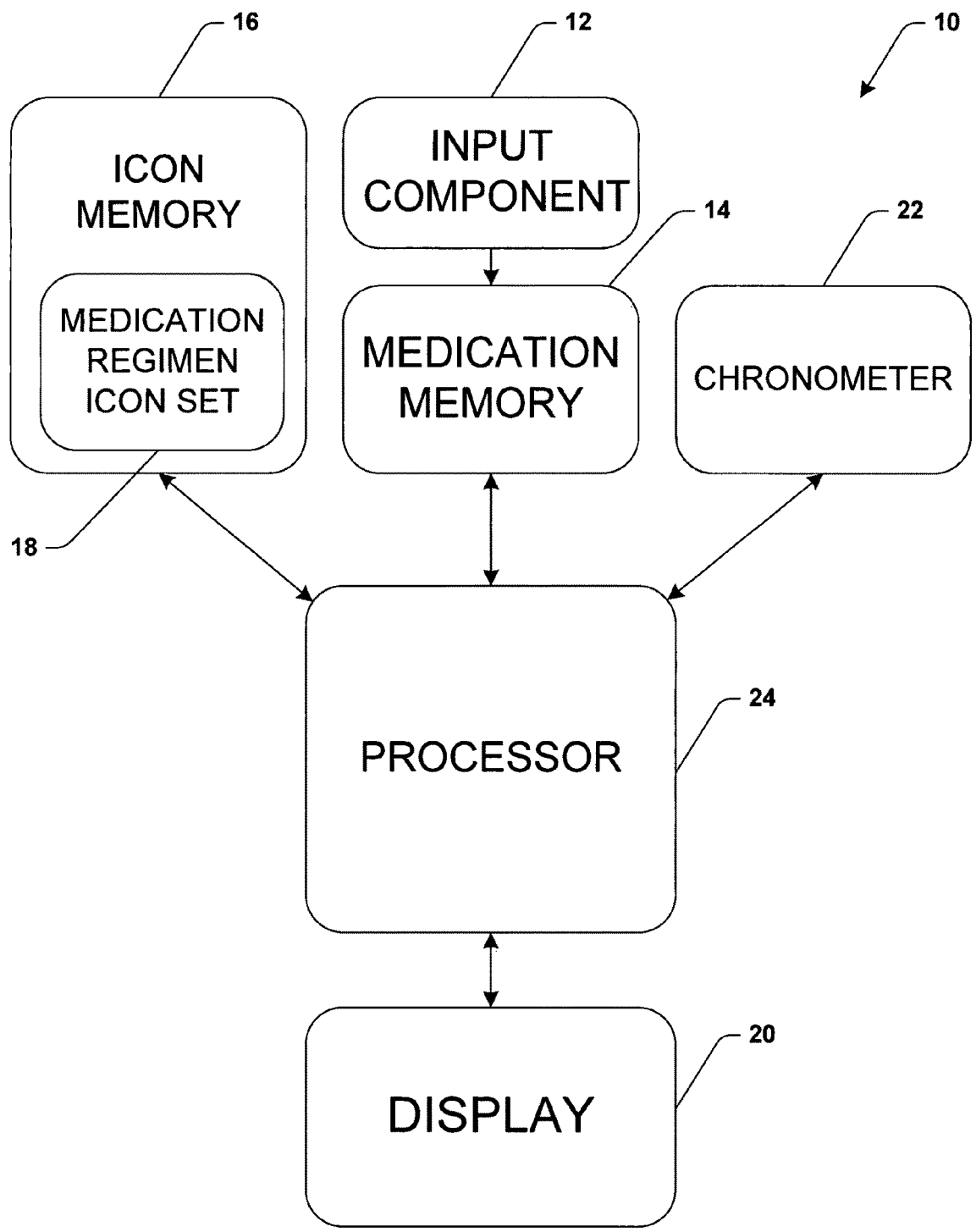
FIG. 1 is an illustration of a device in accordance with the present disclosure.

The following terms used herein are suggested to have the following meanings. This is not intended as an exhaustive list of defined terms, but only as an interpretive aide for facilitating the reading and comprehension of the disclosure described herein. The definitions provided herein are intended to be coupled with the other sources of interpretive guidance for these terms, such as context, common usage in the field of art, and ordinary usage in the English language.

"Healthcare" and "healthcare service" are suggested to mean a service provided to a recipient of healthcare that relates to the health, functionality, and/or physical and/or mental well-being of the recipient. Such services may derive from one or several of the myriad recognized fields of healthcare, including, for instance, allopathic medicine, osteopathic medicine, physical and/or occupational therapy, dentistry, chiropractic medicine, hospice or home healthcare, and pharmaceuticals.

"Caregiver" is suggested to mean a provider of a healthcare service to an individual. "Caregiver" may include any type of healthcare practitioner, including, for instance, a physician, nurse, physical or occupational therapist, chiropractor, dentist, or home healthcare worker. The caregiver may also be a non-professional individual who is involved in providing a healthcare service to the individual, such as a relative, friend, or cohabitant. In a broader context, "caregiver" may include other parties involved in the dispensing of medication to an individual, such as a pharmacist, drug manufacturer, or insurance agent. In the case of self-administered healthcare, the caregiver may be the individual. "Caregiver" may also refer collectively to a plurality or team of such providers, either working together (e.g., a physician and a nurse) or separately (e.g., a physician and a pharmacist.)

"Icon" is suggested to mean a graphic symbol and/or word whose word form represents and/or suggests its meaning.

"Icon set" is suggested to mean a set of icons that together represent some common features of a particular area of healthcare.

"Individual" is suggested to mean a recipient of healthcare service provided by a caregiver. In the case of self-administered healthcare, the individual may also be the caregiver.

"Medication" is suggested to mean a composition of matter administered to an individual in order to prevent, suppress, cure, ameliorate, and/or alleviate an undesirable health condition. Medication may, but need not, be limited to a prescription-restricted pharmaceutical, but may also include (for example) over-the-counter drugs, supplements, and vitamins.

"Medication data set" is suggested to mean a set of data pertaining to a medication regimen, including data pertaining to a medication instruction (such as a medication instruction annotation) and data pertaining to a medication event (such as a medication event annotation.)

"Medication event" is suggested to mean an instance when a medication instruction is to be followed by the individual.

"Medication event annotation" is suggested to mean an annotation about a medication event, such as a symptom experienced by an individual upon an instance of taking a dose of medication.

"Medication instruction" is suggested to mean an instruction by a caregiver to the individual for taking a dose of medication in accordance with the medication regimen. Sometimes, the medication instruction includes a specific date and time at which the dose should be taken.

"Medication instruction annotation" is suggested to mean an annotation about a medication instruction, such as a direction to take the medication on a full stomach.

"Medication prescription refill message" is suggested to mean a message pertaining to a quantity of doses of medication to be provided to the individual in accordance with the medication regimen. Examples of such messages include (without limitation): a notice of the current quantity of medication in the individual's possession; or a request sent to a caregiver (including, without limitation, a pharmacist or a physician) to provide a quantity of doses of medication; and a request sent to a caregiver to authorize the renewal of a medication.

"Medication regimen" is suggested to mean a course of medication recommended by a caregiver for an individual in order to prevent, suppress, cure, ameliorate, and/or alleviate an undesirable health condition.

"Medication regimen icon set" is suggested to mean an icon set that together comprise a predominantly pictorial lexicon for describing the formulation, prescription, and administration of medication to an individual. Some examples of concepts expressed by the medication regimen icon set include (without limitation): a physical condition that the medication is intended to address (e.g., a cardiac condition or a diabetic condition); a formulation of the medication (e.g., a pill or a fluid); a device for administering the medication (e.g., a syringe or an eyedropper); a time at which the medication is to be administered (e.g., morning or evening); and a frequency at which the medication is to be administered (e.g., hourly or daily.) This list is not intended to be exhaustive, but to describe some of the concepts that a medication regimen icon set might express.

"Palette" is suggested to mean a data entry element of a user interface, comprising a circle containing a radially arranged set of icons that represent options for valid input. In one instance, the palette simultaneously displays all of the options for valid input; in another instance, the palette displays a subset of the icon set, along with a button (e.g., labeled "Next" or a right arrow) for displaying a different subset of the icon set.

"Unit box" is suggested to mean a data display element of a user interface that pertains to a data record, where the data display element comprises a set of icons selected from a larger icon set in order to display the data record in a predominantly icon form. The icons are arranged on the unit box according to a template for the type of data record, such that all unit boxes based on the same type of data record will similarly arrange the icons in order to achieve a consistent visual aspect.

DETAILED DESCRIPTION

One or more aspects of the present disclosure are described with reference to the drawings, wherein like reference numerals are generally utilized to refer to like elements throughout, and wherein the various structures are not necessarily drawn to scale. In the following description, for purposes of explanation, numerous specific details are set forth in order to provide a thorough understanding of one or more aspects of the present disclosure. It may be evident, however, to one skilled in the art that one or more aspects of the present disclosure may be practiced with a lesser degree of these specific details. In other instances, well-known structures and devices are shown in block diagram form in order to facilitate describing one or more aspects of the present disclosure.

As discussed above, health-related information can be communicated in a more consistent and language-independent manner by the use of an icon set, where the icons are of predominantly pictorial form and are recognizable representations of medication instructions. The present disclosure recommends a device that communicates with the individual and the caregiver through the display of such an icon set, and also the method of using such a device in order to facilitate compliance with a healthcare regimen.

A device in accordance with the present disclosure is illustrated in FIG. 1. The device 10 comprises an input component 12 for receiving the medication instructions for the medication regimen. The device also comprises a medication memory 14, which stores the medication instructions received by the input component, and an icon memory 16, which contains the medication regimen icon set 18. The device also comprises a display 20, such as an LCD, LED, projector, etc. Finally, the device also comprises a processor 24, which monitors the medication instructions in the medication memory 14, and generates a medication reminder message by displaying on the display 20 one or more icons from the medication regimen icon set 18 that pertain to the medication instruction.

In one set of embodiments, such as the embodiment illustrated in FIG. 1, the device also comprises a chronometer 22. In this embodiment, the processor 24 also monitors the chronometer 22, and uses the information provided by the chronometer 22 to determine when to generate the reminder message(s) for each medication instruction. This information may either be precisely monitored and displayed, e.g. in accordance with an instruction to take a certain medication at 4:00 P.M., or may be more coarsely monitored to generate the reminder message in a broader time frame, e.g. in accordance with an instruction to take a certain medication in the evening.

Figure 2:
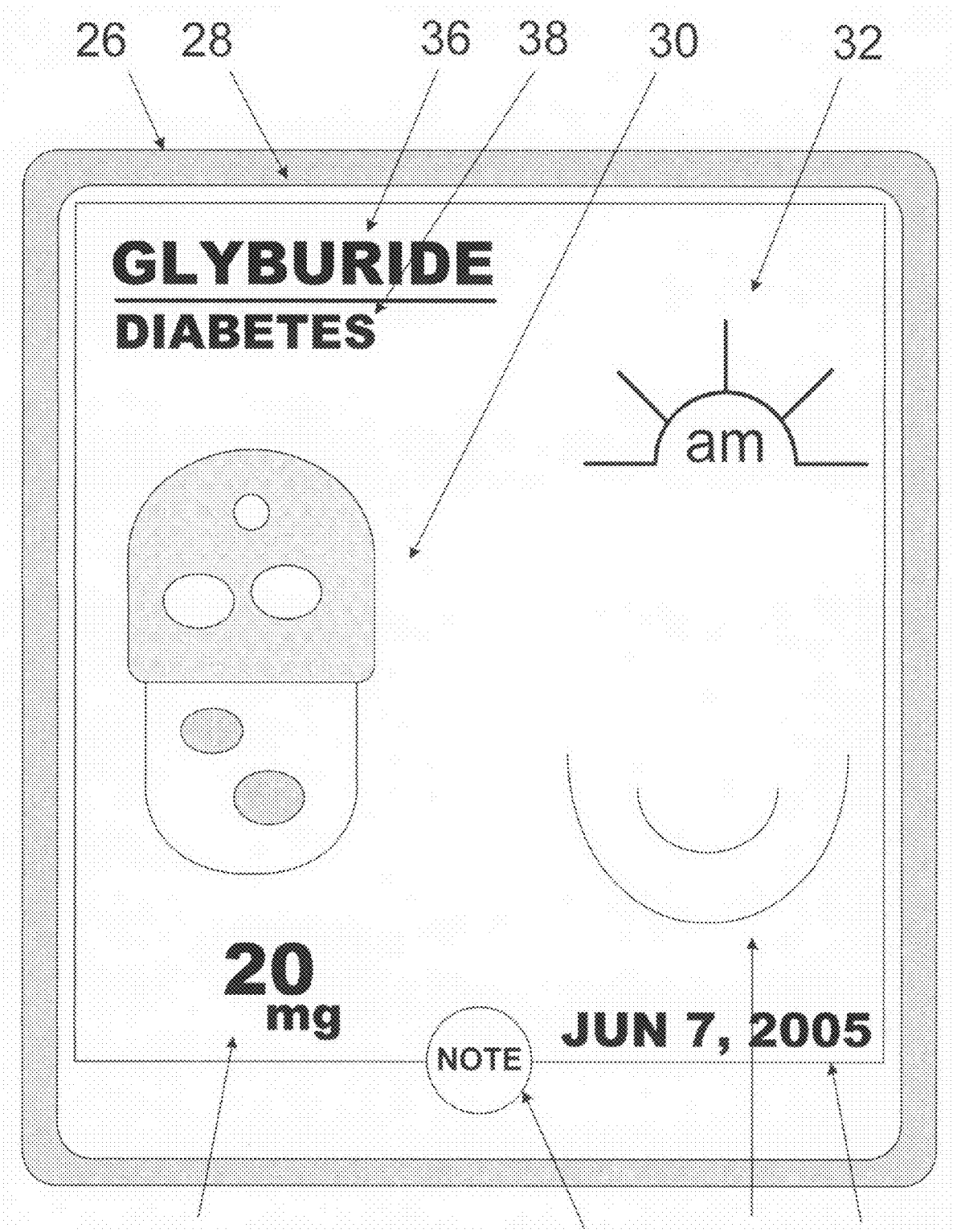
FIG. 2 is an illustration of another device in accordance with the present disclosure.

An illustration of a medication device producing such a message is shown in FIG. 2. The device 26 comprises a display 28 that displays a medication reminder message in a predominantly icon-based form. This message may contain an icon 30 illustrating the medication (e.g., a capsule), an icon 32 illustrating the time of day in which the medication is to be taken (e.g., in the morning), and an icon 34 illustrating the method by which the medication is to be taken (e.g., orally.) Information that is difficult to represent using a pictorial icon may be represented in text form, such as the name of the drug 36, the condition that the drug is prescribed to address 38, the dosage of the drug 40, and the current date 42. However, the medication reminder message should be predominantly icon-based, in furtherance of the advantages suggested herein.

In the embodiment illustrated in FIG. 2, the device 26 presents the information in the form of a unit box, which is a user interface element comprising icons that represent a medical concept. For a class of medical concepts, the unit box presents the details of the concept by showing information, predominantly icons, in specific areas. For instance, a unit box representing any medication instruction (such as shown in FIG. 2) might contain an icon 30 representing the formulation of the medication at center left, an icon 32 representing the time of day at top left, and an icon 34 representing the method of administering the medication at lower left. The text labels 36, 38, 40, 42 are also presented in areas designated for these specific details. The unit box also features a "Note" button 44 which, if activated, presents additional information about the concept. Thus, the unit box user interface element serves as a template for presenting similar kinds of health-related information in a similar, well-defined way, and using an icon set that illustrates the concept in a standardized, recognizable, language-independent manner.

Turning now to the input component of the medication device, it is suggested that many types of input devices may satisfy this function. The input device may be one or more buttons positioned on the device, e.g., a set of buttons that comprise a hardware keyboard. The input component may be a pointing device, such as a mouse or joystick. The input component may be a touchscreen interface that receives touch input.

The user input may be handled in many ways to facilitate the translation of user input into logical instructions. The device may show on the display a keyboard, and may map user input to the keys of the keyboard, in order to function as a software keyboard. Alternatively, the device may feature a handwriting recognition component for parsing the user input from handwriting into written text, and may then parse the written text into medication instructions. The handwriting input in this instance may be either a natural language, or a gesture-based lexicon, such as the gesture-based date entry methods that are common on stylus-based personal data assistant (PDA) devices.

Figure 3:
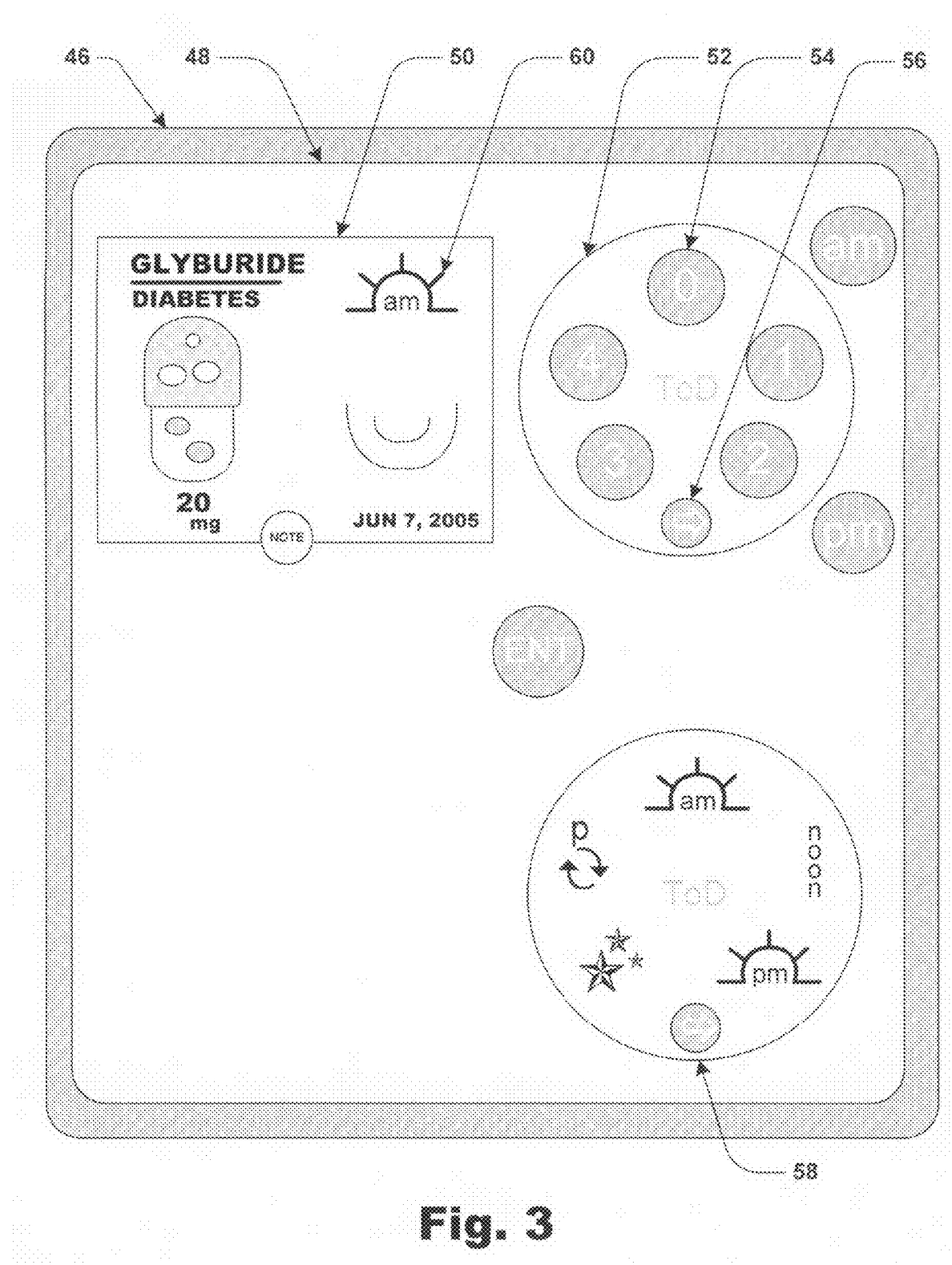
FIG. 3 is an illustration of yet another device in accordance with the present disclosure.

Alternatively, the device may display a set of user interface elements, and may derive input based on the user's interactions with these user interface elements. One example of such an interaction is illustrated in FIG. 3, in which the device is prepared to receive user input pertaining to the time of day for taking a medication dose. In this illustration, the device 46 has a display 48 featuring two types of user elements: a unit box 50, which appears and functions as described above, and two palettes, such as 52.

A palette is a user interface element for accepting user input as a subset of a variety of options. As illustrated in FIG. 3, the palette is centrally labeled to indicate the type of data entry solicited. The data entry options are presented in predominantly icon form 54, and are arranged radially in an enclosing circle. The number of options displayed in the palette is kept small—e.g., five—in order to avoid crowding. If additional options are available, a "Next" arrow 56 is displayed that, if activated, will cause the palette to display additional options. An icon selection may be evaluated as user input, either immediately upon selection or following a confirmation step, e.g., activating an "Enter" button.

In the device of FIG. 3, the user interface comprises a unit box 50 and two palettes 52, 58. The unit box 50 displays the details of a medication instruction, and the palettes 52, 58 allow the user to select or alter the options for one detail. In this case, one palette 52 solicits input as to the hour for the reminder, and another palette 58 solicits input as to the general time of day for the medication instruction. Once these options are selected, the "time of day" icon 60 of the unit box 50 will update to reflect the altered medication instruction.

In another embodiment, the medication device may receive audio user input via a microphone. As one example, the device may feature a voice recognition component for parsing the audio input from voice input into spoken text. The device may then process spoken text may then be parsed into medication instructions.

In another embodiment, the medication device may receive medication instructions not from user input, but from another electronic device. In this embodiment, the medication instructions may be programmed into a separate device, e.g. a personal computer, and then electronically transmitted to the medication device through a communications interface. Many well-known types of communications interfaces may be used for this purpose, such as: a telephonic modulator/demodulator (modem), a Universal Serial Bus (USB) adapter, an infrared (IR) receiver, a network adapter, a wireless network device such as an 802.11-class network adapter, or a cellular mobile communication device.

In one set of embodiments, the individual and/or non-professional caregivers perform the entry of information into the device. In another set of embodiments, information is entered only by caregivers comprising healthcare professionals, and the individual and non-professional caregivers may not enter information, but can only read the information. The latter set of embodiments has several advantages. A healthcare professional may have more accurate and up-to-date information about the medication regimen than the individual or a non-professional, and may be more familiar with its dispensing, symptoms, and targets. The healthcare professional may be better able than the individual or a non-healthcare professional to evaluate the results of the medication regimen and, to make adjustments. It may be optimally efficient for the healthcare professional to program the device with medication instructions at the same time as loading the medication chambers with medication.

In addition to displaying icons, the medication device might supplement the medication reminder message with additional information. In one embodiment, the medication device supplements the reminder message by displaying additional text, e.g., text captions that explain the concept illustrated by the icons (which may be particularly useful for training new users of the medication regimen icon set as to the meanings of the icons.) In another embodiment, the medication device supplements the reminder message by generating sound, such as an audible alarm or a verbal statement. In yet another embodiment, the medication device supplements the reminder message by generating tactile feedback, such as vibration. In yet another embodiment, the medication device supplements the reminder message by transmitting a message to another electronic device, e.g., by sending a text message to a cellular phone, text pager, or Blackberry device.

Figure 4:
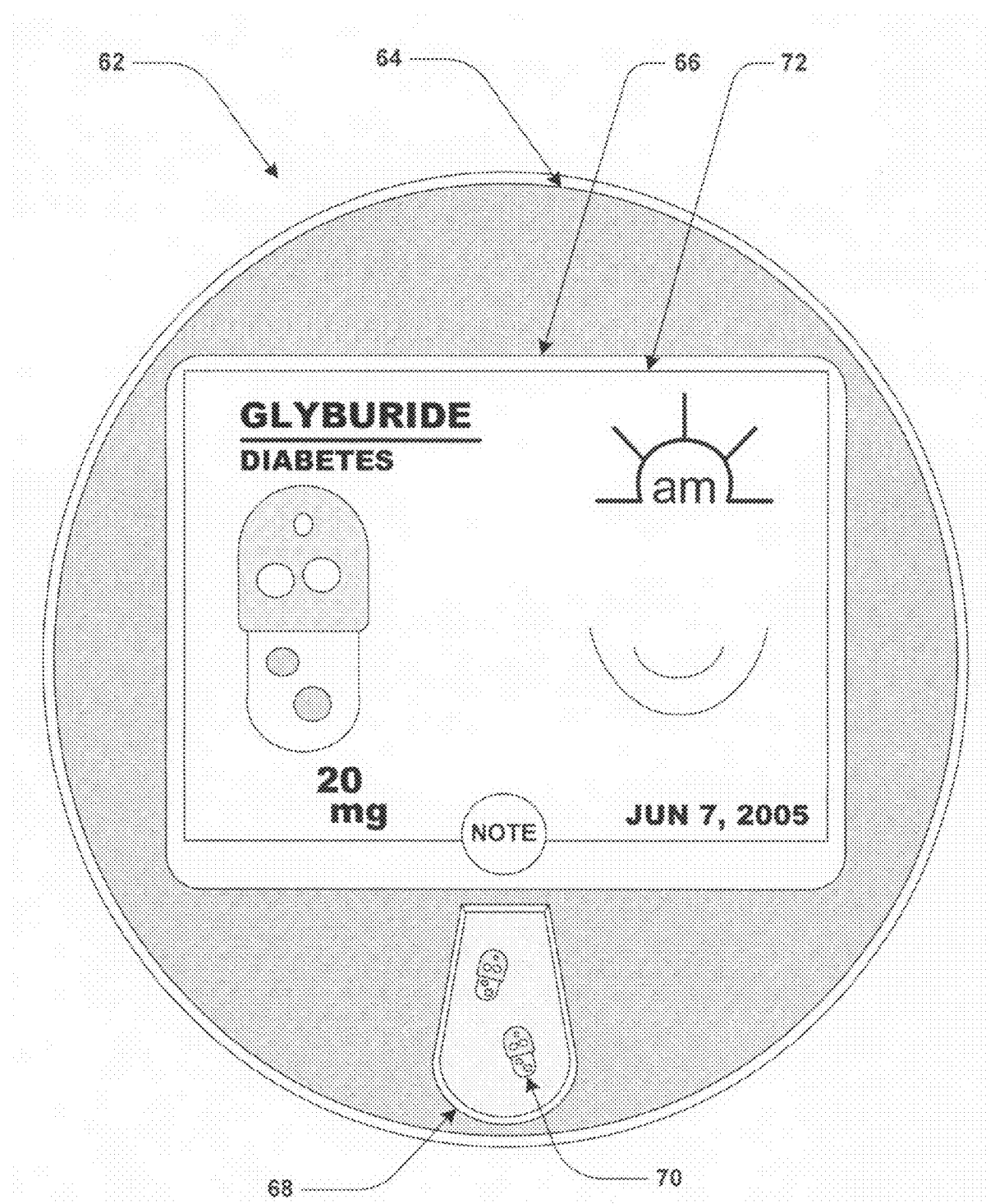
FIG. 4 is an illustration of yet another device in accordance with the present disclosure.

In another set of embodiments, in addition to generating the medication reminder message, the medication device may feature a medication chamber that contains a dose of the medication, and the medication reminder message may reference the medication chamber. The device may contain a plurality of such chambers, and the medication reminder message may reference the chamber corresponding to the current medication instruction. As another example, as illustrated in FIG. 4, the device 62 may feature a top surface 64 containing the display 66 containing a window 68. The medication chambers may be positioned radially underneath the top surface, and the top surface may be rotatable, so that the window selectively exposes one of the medication chambers. During a medication event, the device 62 may cause the display 66 to generate a medication reminder message 72, e.g. in the form of a unit box, and may also position the window 68 to expose the medication chamber containing the medication dose 70 corresponding to the medication instruction. As one example, the device 62 may feature a motor (not shown) that the processor controls to rotate the top surface 64 in order to position the window 68 over the medication chamber referenced by the medication instruction. As another example, the top surface 64 may be freely rotated by the individual, and the medication reminder message 72 may include an arrow to indicate which medication chamber the individual should access in order to expose the medication dose 70 referenced by the medication instruction.

This set of embodiments may include other features. In one set of embodiments of the device and its method of use, the individual is instructed to load the medication chambers with medication doses in accordance with the medication regimen. In another example, the caregiver may load the medication chambers with medication doses in accordance with the medication regimen. In this latter example, the loading of the device may be solely performed by the caregiver (e.g., a physician, nurse, pharmacist, drug manufacturer, etc.), and the individual may be prevented from accessing the medication. This set of embodiments is useful for preventing a variety of medication regimen errors by the individual, such as taking the wrong medication, taking an incorrect dose of medication, or taking a medication dose at an incorrect time.

The embodiments described hereinabove that limit individual access to medication doses may be facilitated by selecting a medication device with hardware that promotes this limitation. As one example, the medication device may feature a processor-controllable medication chamber lock that prevents the individual from accessing each medication dose except in accordance with a medication instruction. An example of this controlled-access medication device may be illustrated by reference to FIG. 4, in which, as discussed above, the device 62 may feature a motor (not shown) operably coupled to the processor (not shown) and the top surface 64, and that may rotate the top surface 64 in order to align the window 68 with one of a plurality of radially disposed medication chambers. Such a device may implement the medication chamber lock as a hardware mechanism that prevents manual rotation of the top surface 64, such that the rotation of the top surface 64 and exposure of the medication doses 70 are controlled by the processor, and in accordance with a medication instruction.

Another feature that may be incorporated in the set of embodiments in which the medication device contains the medication doses is a medication dosing component that allocates and dispenses a quantity of the medication in accordance with the medication instruction. As an example, the medication may be provided in the form of a liquid, and the medication chamber may be loaded with sufficient liquid medication for several medication doses. During the medication event, the medication device may allocate a specific quantity of the liquid medication in accordance with the medication instruction, which may be dispensed to the individual.

Figure 5:
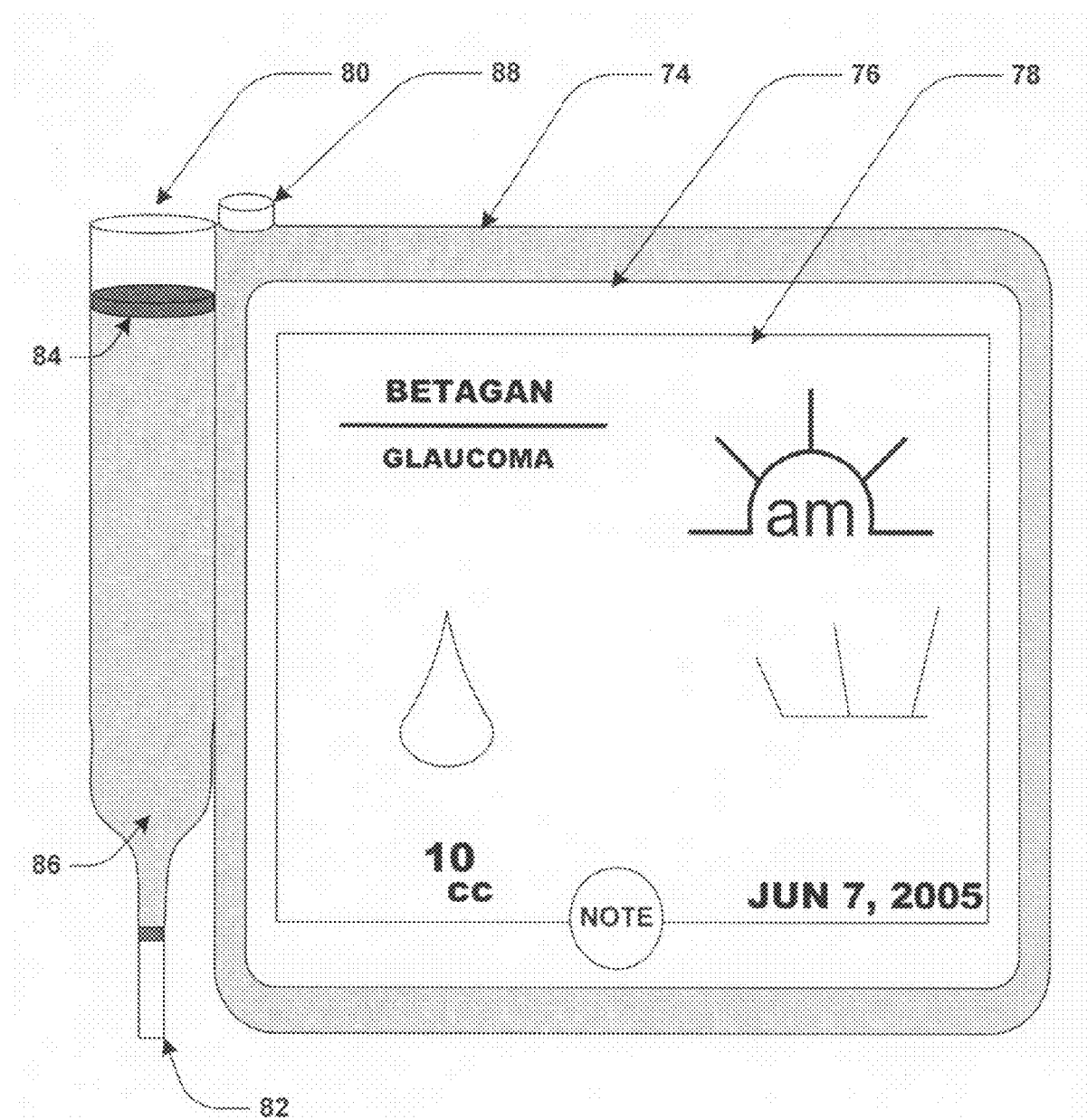
FIG. 5 is an illustration of yet another device in accordance with the present disclosure.

Yet another feature that may be incorporated in the set of embodiments in which the medication device contains the medication doses is a medication administration component for administering the medication dose to the individual. An example of such a device is illustrated in FIG. 5, in which the medication device 74, in addition to featuring a display 76 that presents a medication reminder message 78 in accordance with a medication instruction, also contains a liquid medication chamber 80 terminating in a dropper 82, and containing a controllable stopper 84 for dispensing a desired quantity of medication 86, which is operably coupled with the processor (not shown.) The embodiment illustrated in FIG. 5 also features a dispense button 88. Upon a medication event, such as a medication instruction for administering eyedrops, the medication device may await user input, e.g. depressing of the dispensing button 88, and may in response operate the stopper 84 to dispense a prescribed dose of medication 86 via the dropper 82. Thus, in addition to reminding the individual of the medication instruction, this embodiment also dispenses and administers the prescribed dose of the medication.

Figure 6:
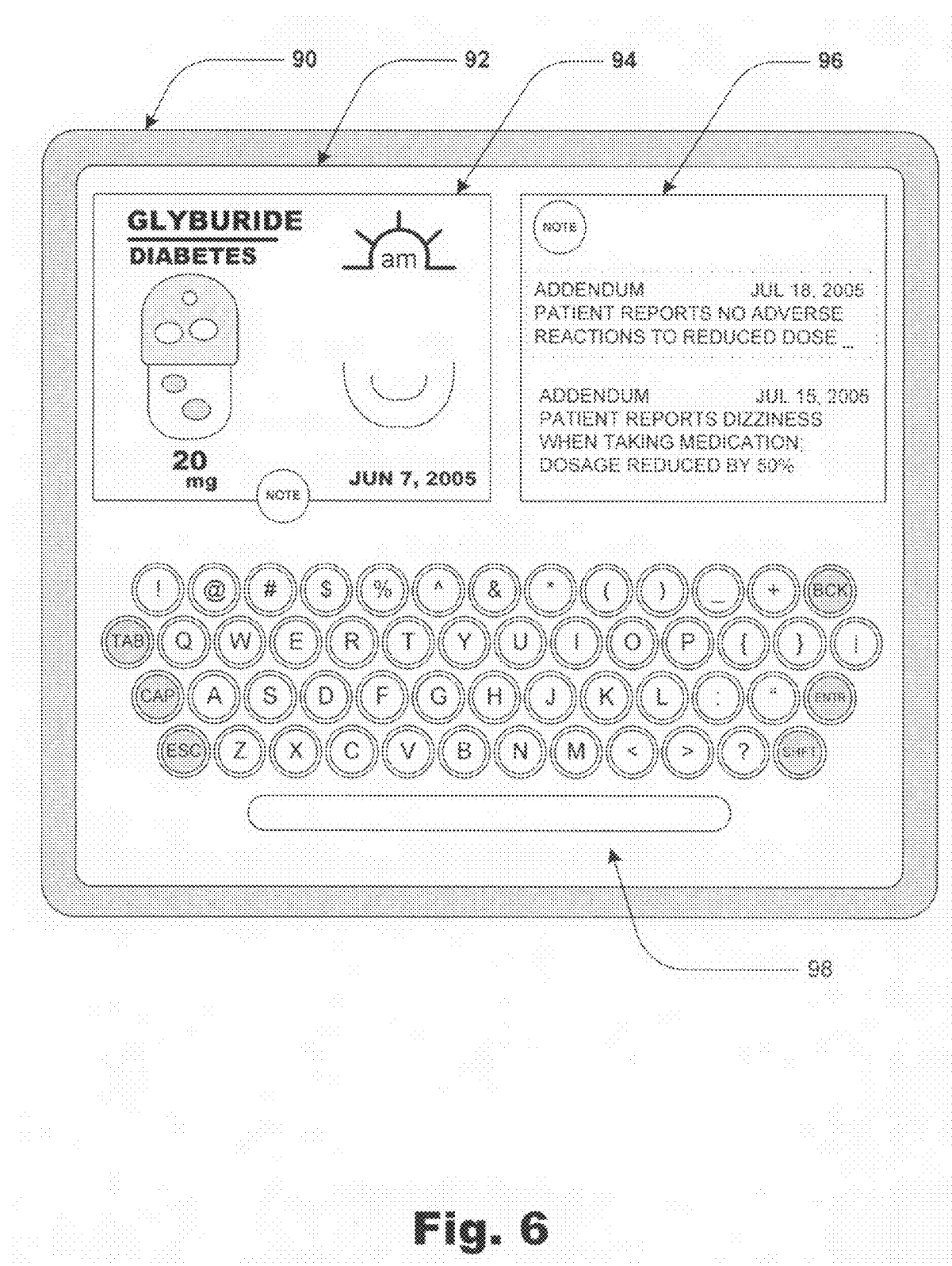
FIG. 6 is an illustration of yet another device in accordance with the present disclosure.

Another feature that may further the purpose of the disclosure is the capability of annotating a medication instruction and/or a medication event. It may be helpful to annotate a medication instruction with additional information, e.g., "take this medication on a full stomach." It may also be helpful to annotate a medication event with information, e.g., "this medication made the individual dizzy." In either case, the annotation may be input by either the individual or the caregiver. Also, the annotation may be provided as input either via the input component that receives the medication instruction, such as those described above, or via a separate input component. Irrespective of the implementation, the medication device stores the annotation and subsequently includes it as output. As one example, the physician may input an annotation about a medication instruction that is subsequently available to the individual as part of the medication reminder message, e.g. by activating the "Note" button of the medication reminder unit box. As another example, the user may input an annotation about a medication event that is stored for later review by the caregiver. The latter example is illustrated in FIG. 6, in which the device 90 features a display 92 that presents a medication reminder message 94, illustrated as a unit box. This device also illustrates a note input region 96 and a software keyboard 98, so that the individual may record an annotation describing his or her condition during the medication event.

The medication device might contain the medication, and may provide a dose of the medication to the individual in accordance with the medication instruction. The medication device may additionally contain a lock mechanism for the medication chamber, in order to limit access to the medication except in accordance with a medication instruction. Further, the medication device may measure and/or administer the dose for the individual (e.g., by incorporating an eyedropper mechanism.)

The medication device might communicate with the caregiver by exchanging information about the medication regimen for the individual. This information, generally referred to as a "medication data set," might include an additional medication instruction, a medication instruction annotation, and/or a medication event annotation. The device might also contain a component for detecting compliance by the individual with the medication instruction (e.g., a sensor that determines whether or not a pill was removed from a chamber in the medication device), and might communicate this information to the caregiver.

In yet another set of embodiments, the medication device may include a communications component for exchanging with the caregiver a medication data set. As with the input component, the communications component may be selected from many well-known types of digital interfaces, such as: a telephonic modulator/demodulator (modem), a Universal Serial Bus (USB) adapter, an infrared (IR) receiver, a network adapter, a wireless network device such as an 802.11-class network adapter, or a cellular mobile communication device. The input component may also serve the function of communications component. The communications component exchanges with the caregiver data about the medication regimen, which is generally referred to herein as a medication data set.

The medication data set may contain many kinds of data about the medication regimen. For example, the medication data set may contain additional or altered medication instructions. A caregiver or a caregiver's computer system may communicate with the medication device in order to provide additional medication instructions. For instance, the medication data set may include additional or altered medication instructions, such as when a prescription is refilled or a medication regimen is adjusted. The medication data set may include a medication instruction annotation, such as new information about a pharmaceutical drug that the caregiver wishes the individual to know and follow. The medication data set may include a medication event annotation, such as a report by the individual of symptoms experienced upon taking a medication dose. The medication data set may include a medication prescription refill message, which may be issued in advance of exhaustion of the medication so that the prescription refill is received in time for continuation of the medication regimen. In all such embodiments, the exchange of the medication data set between the medication device and the caregiver facilitates communication and monitoring of the individual's medication regimen, and thus furthers the advantages of the present disclosure.

One particular embodiment that combines features of several embodiments suggested above is a medication device including both a medication chamber, and a communications component. In this case, the medication device may also feature a detection component that is operably coupled to the medication chamber for detecting compliance of the individual with the medication instruction. For instance, the detection device may be a pressure sensor that detects the removal of a medication dose from the medication chamber. The medication device may then transmit to the caregiver, via the communications component, a medication instruction compliance message that corresponds to the medication instruction. The caregiver's computer system might be configured to process the message and assemble a record of the compliance of the individual with the medication regimen.

Figure 7:
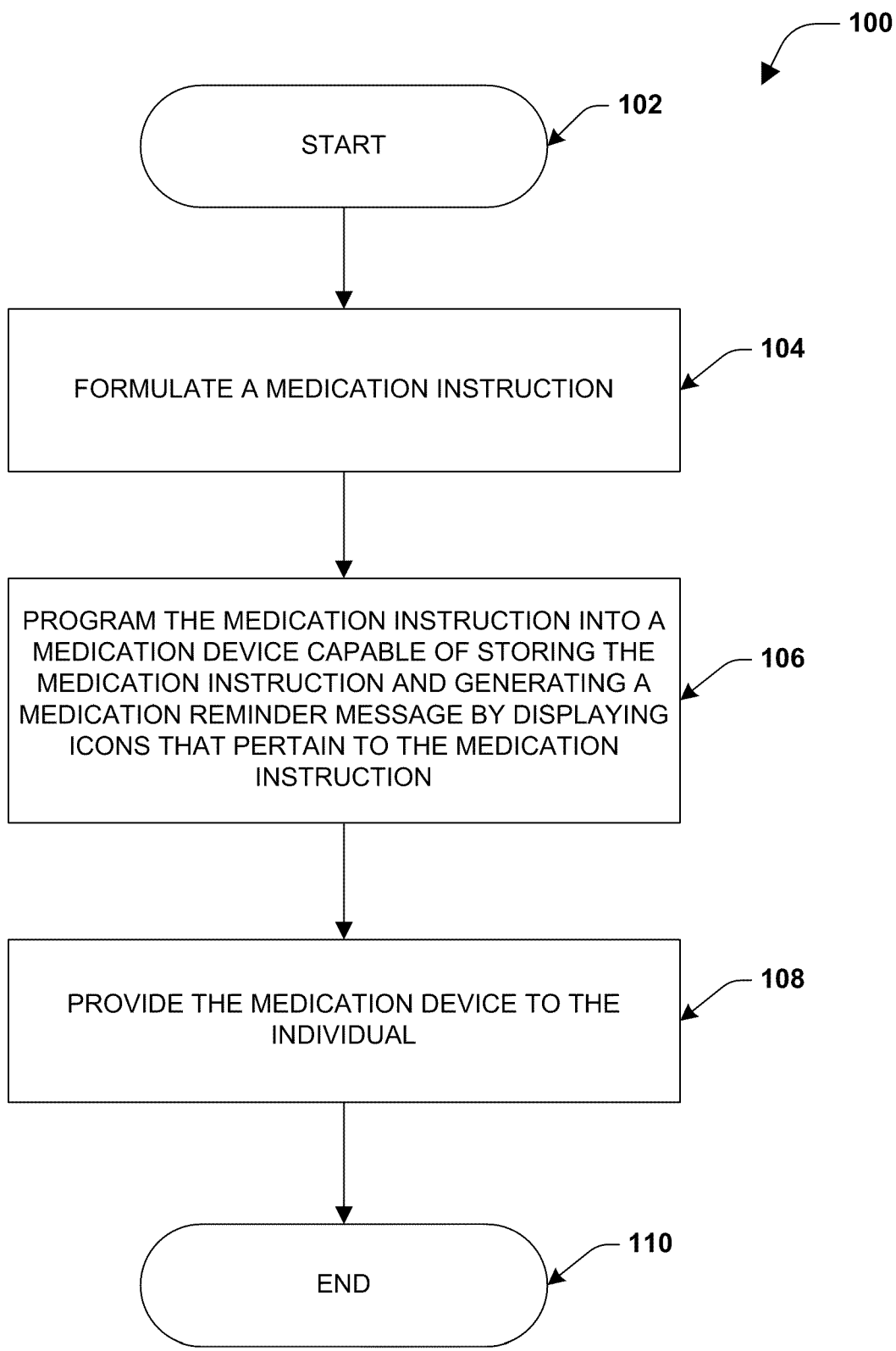
FIG. 7 is an illustration of a method in accordance with the present disclosure.

The disclosure also includes the method of facilitating compliance by an individual with a medical regimen. This method involves the utilization of a device such as described hereinabove. This method, as illustrated in FIG. 7, 100 begins at 102, and comprises the steps of formulating a medication instruction 104; programming the medication instruction into a medication device capable of storing the medication instruction and generating a medication reminder message by displaying icons that pertain to the medication instruction 106; and providing the medication device to the individual 108, after which the method ends 110. The provision of such a medication device, programmed according to the medication regimen, to the individual will promote compliance by the individual with the medication regimen.

Just as the medication device is described hereinabove has having many embodiments with varying features, this method may be augmented by selecting medication devices having such features, and by using the medication device in different ways.

In one embodiment of this method, the programming of the medication device is performed by the individual, such as when a caregiver simply provides the unprogrammed medication device and a medication regimen. In another embodiment, the programming of the medication device is performed by the caregiver, who then provides the programmed medication device to the individual. The former embodiment may reduce the business process overhead for the caregiver (and prevents liability for incorrectly programmed devices), while the latter embodiment may further increase compliance with the medication regimen.

Another set of embodiments of this method involve medication devices that accept medication instruction annotations. In one embodiment of this method, the annotation of the medication instruction is performed by the individual, such as when the individual wishes to include personal notes in future medication reminder messages (e.g., "I feel better when I take this with water.") In another embodiment of this method, the annotation of the medication instruction is performed by the caregiver, such as when the caregiver wishes to include additional notes about a medication regimen while programming the medication device.

Still other sets of embodiments of this method involve medication devices that feature a medication chamber, and where a medication dose is loaded into the medication chamber. In one set of embodiment of this method, the loading is performed by the individual, such as when the caregiver who programs the medication device is different from the caregiver who supplies the medication. In another set of embodiments of this method, the loading is performed by the caregiver, such as when a pharmacist or a medical drug manufacturer provides a prescription medication to an individual in a pre-loaded medication device. Embodiments within this latter set may also involve medication devices having a controllable medication chamber lock, which may limit access to the medication dose as discussed hereinabove. Embodiments within this latter set may also involve a medication administering component, and the method may include administering the medication dose to the individual in accordance with the medication instruction, as discussed hereinabove.

Still another set of embodiments of this method involve medication devices that accept medication event annotations. In one embodiment of this method, the annotation of the medication event is performed by the individual, such as when the individual wishes to record a sensation experienced during a medication event (e.g., "this medication made me feel dizzy.") In another embodiment of this method, the annotation of the medication instruction is performed by the caregiver, such as during an office visit where medication is administered (e.g., "patient visited and was given intramuscular injection of 10 cc of medication.")

Still another set of embodiments of this method involve medication devices that feature a communications component for exchanging a medication data set with the caregiver, as described hereinabove. The medication data set exchanged in these methods may include an additional or updated medication instruction (e.g., upon the refill or alteration of a prescription regimen.) The medication data set may include a medication instruction annotation (e.g., when the caregiver wishes to provide the individual with additional information about a medication instruction.) The medication data set may include a medication event annotation (e.g., when the individual wishes to record a sensation experienced during a medication event.) The medication data set may include a medication prescription refill message (e.g., a request to a caregiver to authorize refill of a prescription when the current prescription is nearing exhaustion.) The medication data set may include a medication instruction compliance message, particularly when the medication device includes a detection component for detecting individual compliance with the medication instruction, as discussed hereinabove. In all such embodiments, the exchange of the medication data set between the medication device and the caregiver facilitates communication and monitoring of the individual's medication regimen, and thus furthers the advantages of the present disclosure.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (assemblies, elements, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising." Also, "exemplary" as utilized herein merely means an example, rather than the best.

What is claimed is:

1. A device for facilitating compliance with a medication regimen formulated by a caregiver for an individual, comprising:
   an input component configured to receive input representing a medication instruction for the medication regimen;
   a medication memory configured to store the medication instruction;
   an icon memory containing a medication regimen icon set comprising icons of predominantly pictorial form that are recognizable representations of medication instructions;
   a display;
   a processor configured to:
      receive at least one medication instruction by:
         presenting on the display at least one palette comprising a radially arranged set of icons selected from the icon memory that represent options for an aspect of the medication instruction and a label indicating the aspect of the medication instruction, and
         upon receiving input from the input component representing a selection in the palette of an icon representing an aspect of a medication instruction, store the medication instruction in the medication memory;
      generate a medication reminder message by displaying on the display icons that together depict the medication instruction, where the icons are selected from the medication regimen icon set in the icon memory; and
      upon receiving input from the input component representing a medication event annotation that pertains to a medication event associated with the medication instruction, store the medication event annotation in the medication memory;
   a communications component for exchanging with the caregiver a medication data set that pertains to the medication regimen;
   a medication chamber that contains a medication dose corresponding to the medication instruction, and where the medication reminder message references the medication chamber; and
   a detection component that is operably coupled to the medication chamber for detecting compliance of the individual with the medication instruction, and also operably coupled to the communications component for transmitting to the caregiver a medication instruction compliance message that corresponds to the medication instruction.

2. The device of claim 1, further comprising a chronometer, and where the processor monitors the chronometer to determine when to display the medication reminder message.

3. The device of claim 1, where the input component comprises one or more buttons.

4. The device of claim 3, where the buttons of the input component comprise a hardware keyboard.

5. The device of claim 1, where the input component comprises a pointing device.

6. The device of claim 1, where the input component comprises a touchscreen interface.

7. The device of claim 6, where the touchscreen interface includes a software keyboard.

8. The device of claim 6, further comprising: a handwriting recognition component for translating handwriting input from the touchscreen interface into text input.

9. The device of claim 1, where the input component comprises a microphone, and further comprising an audio recognition component for translating audio input from the microphone into text input.

10. The device of claim 9, where the audio recognition component is a speech recognition component.

11. The device of claim 1, where the input component receives a medication instruction annotation that pertains to the medication instruction.

12. The device of claim 11, where the medication reminder message is supplemented by displaying the medication instruction annotation.

13. The device of claim 1, further comprising:
a speaker, and
an audio component for supplementing the medication reminder message by playing audio.

14. The device of claim 1, further comprising: a tactile feedback component for supplementing the medication reminder message by generating a tactile signal.

15. The device of claim 14, where the tactile signal is vibration.

16. The device of claim 1, further comprising: a transmitter for supplementing the medication reminder message by transmitting an electronic message to another electronic device.

17. The device of claim 1, further comprising: a medication chamber that contains a medication dose corresponding to the medication instruction, and where the medication reminder message references the medication chamber.

18. The device of claim 17, where the medication dose is loaded into the medication chamber by the individual.

19. The device of claim 17, where the medication dose is loaded into the medication chamber by the caregiver.

20. The device of claim 19, further comprising: a controllable medication chamber lock, where the processor controls the medication chamber lock to limit access to the medication dose according to the medication instruction.

21. The device of claim 17, further comprising: a medication dosing component for allocating and dispensing a quantity of the medication according to the medication instruction.

22. The device of claim 17, further comprising: a medication administration component for administering the medication dose to the individual according to the medication instruction.

23. The device of claim 1, where the medication data set includes a medication instruction.

24. The device of claim 1, where the medication data set includes a medication instruction annotation.

25. The device of claim 1, where the medication data set includes a medication prescription refill message.

26. The device of claim 1, the processor configured to display on the display the icons that together depict the medication instruction in a unit box representing no more than one medication instruction and comprising at least one icon positioned within the unit box according to a template.

27. The device of claim 26:
the medication memory storing a first medication instruction having a first medication event on a date and a second medication instruction having a second medication event on the date; and
the processor configured to display:
a first unit box comprising at least one icon positioned within the unit box according to a template and representing the first medication event of the first medication instruction, and
a second unit box comprising at least one icon positioned within the unit box according to a template and representing the second medication event of the second medication instruction.

* * * * *